United States Patent [19]

Mastico et al.

[11] Patent Number: 5,450,015
[45] Date of Patent: Sep. 12, 1995

[54] APPARATUS FOR MEASURING IMPEDANCE TO DETERMINE A PROPERTY OF A MATERIAL

[75] Inventors: Robert A. Mastico; Robert R. Moline, both of Braintree, Mass.

[73] Assignee: Forte Technology, Inc., Norwood, Mass.

[21] Appl. No.: 201,514

[22] Filed: Feb. 24, 1994

[51] Int. Cl.6 .................. G01N 27/22; G01R 27/26
[52] U.S. Cl. ................... 324/665; 324/672; 324/679
[58] Field of Search ............... 324/664, 665, 672, 679, 324/694, 704, 705, 713

[56] References Cited

U.S. PATENT DOCUMENTS

| | | | |
|---|---|---|---|
| 3,020,476 | 2/1962 | Jacoby | 324/679 X |
| 4,370,611 | 1/1983 | Gregory et al. | 324/679 X |
| 4,568,875 | 2/1986 | Piso et al. | 324/665 X |
| 4,845,421 | 7/1989 | Howarth et al. | 324/665 X |
| 5,068,618 | 11/1991 | Fry et al. | 324/706 |
| 5,371,469 | 12/1994 | Anderson | 324/705 |

*Primary Examiner*—Kenneth A. Wieder
*Assistant Examiner*—Glenn W. Brown
*Attorney, Agent, or Firm*—John E. Toupal; Harold G. Jarcho

[57] ABSTRACT

An impedance measurement system including a series circuit having a reference impedance leg and a measurement leg, the measurement leg including first and second spaced apart electrodes defining a region for receiving a sample of material to be tested; an oscillator circuit connected in parallel with the series circuit and providing a reference voltage and a signal voltage proportioned to the impedance of the measurement leg; and a detector circuit producing an output voltage proportional to changes between the reference voltage and the signal voltage.

15 Claims, 2 Drawing Sheets

APPARATUS FOR MEASURING IMPEDANCE TO DETERMINE A PROPERTY OF A MATERIAL

BACKGROUND OF THE INVENTION

This invention relates generally to the measurement of selected properties of materials and, more particularly, to the impedance measurement of such properties.

When dealing with materials it is often necessary to measure such properties as moisture content, composition, density and the like. Moisture content, for example, influences both the physical and chemical behavior of materials. In a physical sense, moisture content contributes to the overall weight of materials and is therefore an important factor in determining their invoice value for shipping purposes. In a chemical sense, moisture content is a factor in process control.

One technique for measuring a selected property of a material makes use of the fact that an electrical constant of the material, such as its dielectric constant, can be indicative of a selected property under test. For example, as the moisture content of a material increases, with other properties held constant, there is a corresponding increase in dielectric constant. In using this technique, it is customary to employ the material as the dielectric of a capacitive test cell. The cell may be calibrated so that an indicated change in capacitance is a measure of moisture content. Typically, an oscillator is employed with the test cell and measurements are made with different spacings between test cell electrodes.

The frequency shift resulting from the changed electrode spacing is indicative of the material's moisture content. In such systems, oscillator drift can create measurement errors. Also, such systems are generally ineffective for lossy materials in which a frequency signal deteriorates. Particular difficulties are encountered with materials having high moisture content of, for example, greater than 20%.

The object of this invention, therefore, is to provide an improved system for measuring predetermined properties of materials.

SUMMARY OF THE INVENTION

The invention is an impedance measurement system including a series circuit having a reference impedance leg and a measurement leg, the measurement leg including first and second spaced apart electrodes defining a region for receiving a sample of material to be tested; an oscillator circuit connected in parallel with the series circuit; an output circuit connected in parallel with the series circuit and providing a reference voltage level and a signal voltage level proportional to the impedance of the measurement leg; and a detector circuit producing an output voltage level proportional to the impedance. The output voltage level provides data regarding predetermined properties of the material being tested.

According to one feature of the invention, the reference impedance leg includes a reference capacitor. The impedance of the material under test and the reference capacitor form a divider circuit that produces voltages useful in measuring moisture content.

According to another feature of the invention, the reference impedance leg further includes a variable resistor. The variable resistor is used to correct phase differences in the compared referenced signal voltages.

According to still another feature of the invention, the variable resistor is connected in series with the reference capacitor. Phase correction is simplified by this circuit arrangement.

According to a further feature of the invention, the detector circuit includes a differential amplifier. The detrimental effects of even small voltage shifts are eliminated by the differential amplifier.

Also encompassed by the invention is a method for determining a property of a material with a system including a series circuit having a reference impedance leg and a measurement leg including first and second spaced apart electrodes defining a region; an oscillator circuit connected in parallel with the series circuit; an output circuit connected in parallel with the series circuit and providing a reference voltage level and a signal voltage level proportional to the impedance of the measurement leg; and a detector circuit for combining the reference voltage level and the signal voltage level and producing therewith an output voltage level proportional to a combination of the reference voltage level and the signal voltage level; the method including the steps of: positioning a material sample in the region; establishing a given spacing between the first and second electrodes; utilizing the output voltage level to determine an initial impedance of the measurement leg with the given spacing between the first and second electrodes; establishing a different predetermined spacing between the first and second electrodes; utilizing the output voltage level to determine a changed impedance of the measurement leg with the predetermined spacing; and comparing the initial impedance with the changed impedance. The comparison is used to determine a certain property of the material under test.

According to features of the above method, the comparing step includes the step of determining the difference between the initial impedance and the changed impedance, and the method also includes the steps of determining a value proportional to the difference, determining the weight of the material sample, and dividing the value by the weight. These steps provide a determination of the sample materials moisture content.

The invention further encompasses a system including a first grounded electrode; a second electrode spaced from the first grounded electrode in a given direction so as to define a region for receiving a material sample; a third grounded electrode spaced from the second electrode in another direction opposite to the given direction; a motive mechanism for selectively varying the spacing between the first and second electrodes; and a sensing circuit connected to the first and second electrodes. The sensing circuit senses the impedance of the material sample to indicate a specific property thereof and the third grounded electrode reduces system noise by eliminating the undesirable effects of an undefined capacitance value existing between the second electrode and surrounding equipment.

According to one feature of the above system, the second and third electrodes form an assembly movable by the motive mechanism. The assembly insures during test operations a uniform spacing between the second and third electrodes.

According to another feature of the invention, the system includes a detector for determining the spacing between the first and second electrodes. Knowledge of the spacing between the first and second electrodes facilitates a determination of moisture content of the material sample.

DESCRIPTION OF THE DRAWINGS

These and other objects and features of the invention will become more apparent upon a perusal of the following description taken in conjunction with the accompanying drawings wherein.

DESCRIPTION OF THE PREFERRED EMBODIMENT

Figure 1:
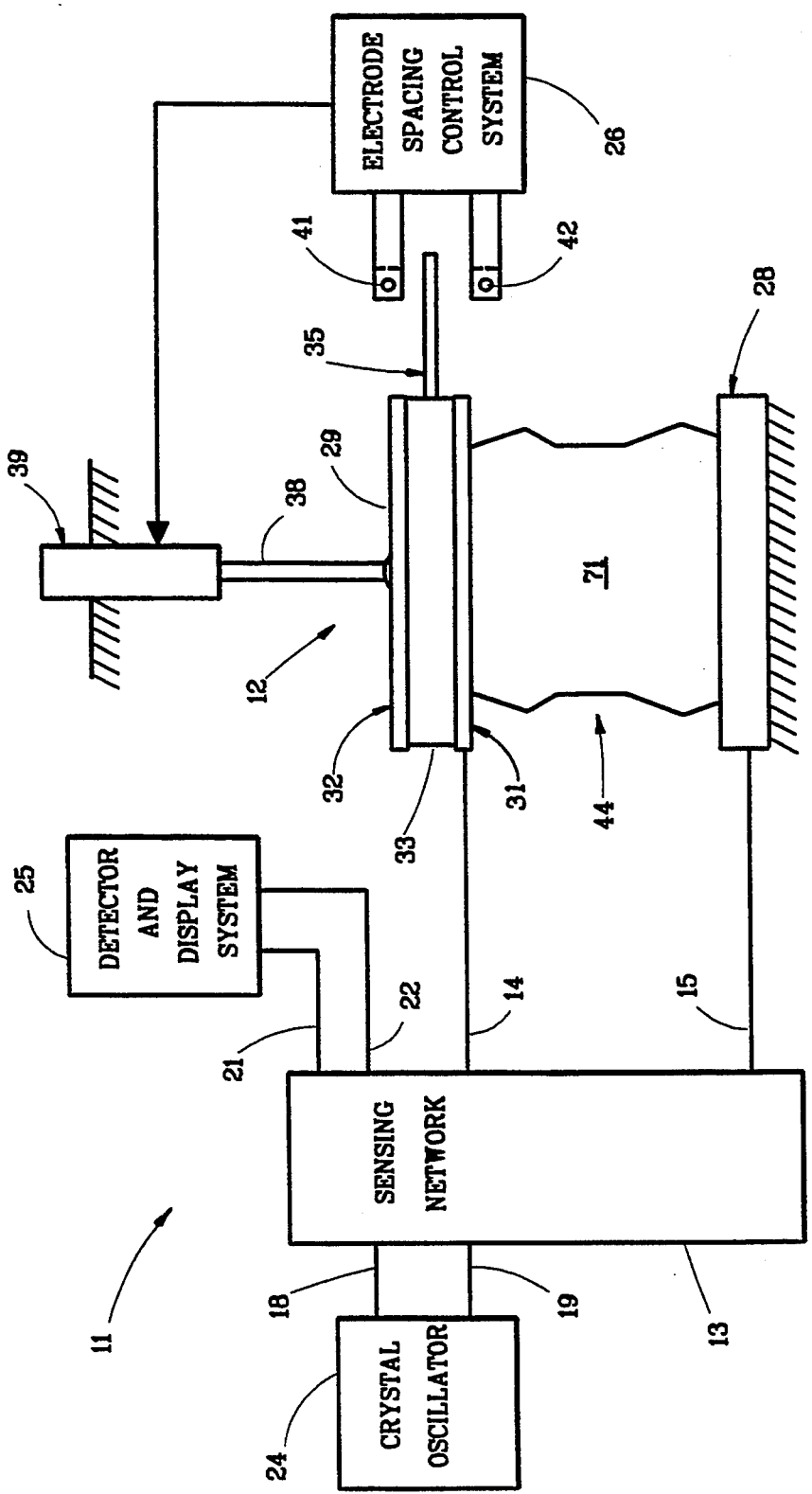
FIG. 1 is a schematic block diagram of the invention.

A moisture measurement system 11 includes an electrode assembly 12 connected to a sensing network 13 by electrical lines 14 and 15. Also connected to the sensing network 13 by, respectively, lines 18, 19 and 21, 22 are a crystal oscillator 24 and a detector and display system 25. The moisture measurement system 11 also includes for the electrode assembly 12 a spacing control system 26.

The electrode assembly 12 consists of a fixed and grounded first electrode 28 and a movable electrode assembly 29. Forming the movable electrode assembly 29 are a second electrode 31 parallel to and spaced from the first electrode 28 and a third electrode 32 separated from the second electrode 31 by electrically insulating material 33. Preferably, the insulating material 33 is a suitable resin in which the second and third electrodes 31, 32 are potted. Also potted into and extending transversely from the assembly 29 is a vane 35. Secured to the movable assembly 29 is a motive mechanism including a piston 38 actuated by a hydraulic cylinder 39.

The spacing control system 26 receives inputs from a pair of photocells 41, 42 disposed adjacent to a region 44 defined between the first and second electrodes 28, 31. In response to inputs from the photocells 41, 42, influenced by proximity of the vane 35, the spacing control system 26 controls operation of the hydraulic cylinder 39 and piston 38 to produce movement of the electrode assembly 29 and thereby establish desired given and predetermined spacings between the first and second electrodes 28, 31.

Figure 2:
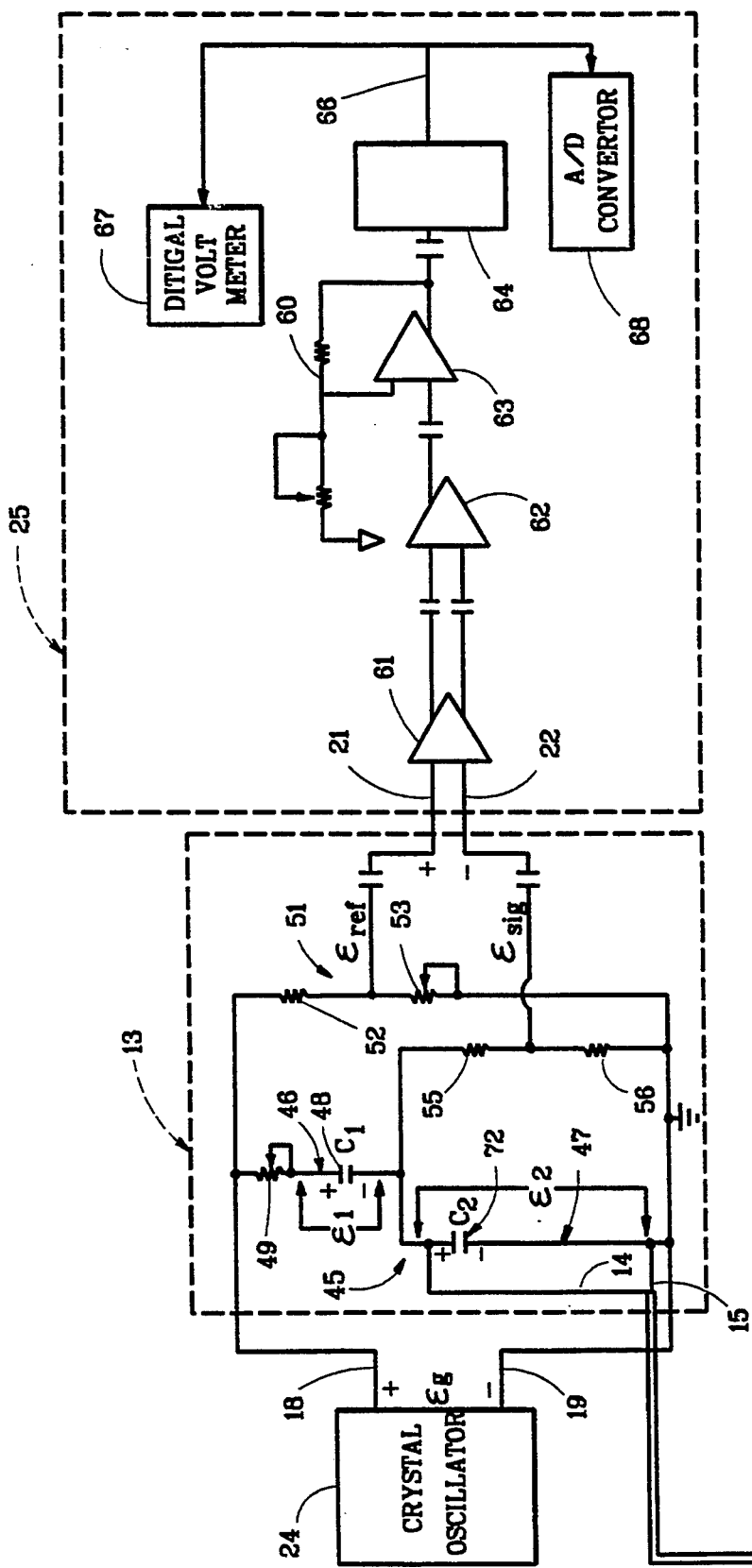
FIG. 2 is an electrical circuit diagram of a portion of the invention shown in FIG. 1.

As shown in FIG. 2, the sensing network 13 includes a series circuit 45 that receives on lines 18 and 19 a signal Eg from the crystal oscillator 24. Forming the series circuit 45 is a reference leg 46 connected in series with a measurement leg 47 that includes the first and second electrodes 28, 31 and the region 44 therebetween. The reference leg 46 is formed by a reference capacitor 48 and a variable resistor 49 connected in series therewith. Established across the reference capacitor 48 is a voltage El. An output circuit 51 includes a reference resistor 52 and an adjustable reference resistor 53 connected in parallel with the series circuit 45 and a pair of signal resistors 55, 56 connected in parallel with the measurement leg 47. The line 21 is connected to a junction between the reference resistors 52, 53 and provides a reference voltage Eref and the line 22 is connected to a junction between the signal resistors 55, 56 and provides a signal voltage Esig. Established between the first and second electrodes 28, 31 is a voltage E2.

The detector and display system 25 includes a differential amplifier 61 that receives the reference voltage $E_{ref}$ and signal voltage $E_{sig}$ on lines 21, 22 respectively. The output of the amplifier 61 provides an input to a single ended output amplifier 62. Receiving an output from the single ended output, amplifier 62 is an input buffer amplifier 63, the gain of which is controlled by a gain control circuit 60. The output of the amplifier 63 is applied to an output amplifier 64 that provides on line 66 an output voltage to both a digital voltmeter 67 and an analog to digital converter 68.

OPERATION

If a sample of pulp, textile fiber or other material is the dielectric and resistive medium in a parallel plate capacitor, an empirical equation that relates the percent moisture content of the material over a small but useful range is: %MC=A log I/W+B+R(T). Where: %MC=Percent Moisture Content; I=Impedance (Capacitive & Resistive); T=Temperature of the Material; W=Weight of the Material; A, B, R=Constants.

If C2 represents the total capacitance (impedance) represented by the lines 14, 15, the electrodes 28, 31 and a sample 71 in the region 44 (FIG. 2), and C1 is the value of capacitor 48 which is fixed but chosen so that the voltage E2 is approximately one half of Eg by the relationship: E2=Eg(C1/(C1+C2)). Then for any change in C2 there will be a corresponding change in E2. For a small region, a small change in C2 will produce a nearly linear change in E2 and since small changes in C2 relate to changes in the impedance of the sample 71 then we have a means to measure changes in the sample which are proportional to the % moisture content of the sample.

Rearranging the equation we have: E2/Eg=C1(C1+C2). Then by measuring both E2 and Eg and using a mathematical ratio of these two voltages, test results are protected from any slight variations which may have been caused by small changes in amplitude of the oscillator voltage Eg.

When energized, the oscillator 24 provides a sine wave whose amplitude and frequency are constant across the series circuit 45 and the associated output circuit 51. The reference capacitor 48 represents a fixed value C1 while capacitor 72 represents a fixed capacitor (impedance) C2 provided by the lines 14, 15 the electrodes 28, 31 and the sample 71. Preferably, the capacitor 48 is selected so that the oscillator voltage Eg is divided about in half across C1 and C2. Initially (with no sample present) the resistors 49 and 53 are adjusted to provide a reference voltage, Eref, which is in phase and just slightly larger than Esig, a voltage proportional to the moisture content of the sample. Also adjustments are made to provide a null voltage at line 66.

The sample 71 then is introduced into the region 44 with a given spacing between the electrodes 28, 31. Introduction of the sample 71 produces an increase in a total, capacitance C2 (impedance) because the sample acts as the dielectric for the capacitor made up of the electrode plates 28, 31. Previously this dielectric was air. The increase in capacitance (impedance) is proportional to moisture content of the sample 71 according to the equation:

$$\% MC = A \log (I/N) + B + R(T)$$

where the symbols represent the values described above.

E2 is decreased by this increase in C2 which produces a decrease in the signal voltage level Esig. Since the level of the reference signal Eref is proportional to Eg and is essentially constant we have an increase in the voltage Eref-Esig which is applied to the differential amplifiers 61, 62. These amplifiers produce an output voltage level proportional to the difference of Eref and Esig and the impedance of the sample 71. The amplifiers 61, 62 also provide gain and common mode noise rejection. The output of 62 is used single ended and applied to the amplifier 63 which provides voltage scaling and acts as an input buffer to the RMS to DC converter 64. The gain of amplifier 63 is adjusted by the control circuit 60 to give the proper full scale voltage at the output of converter 64 which is then applied to the voltmeter 67 and the A/D converter 68. This first reading from the detector 25 represents an initial value of the capacitor C2 with the given electrode spacing.

Next the sample 71 is left in place within the region 44 and a smaller predetermined spacing is provided between the electrode plates 28, 31 by the piston 38 under control of the control system 26. The smaller electrode spacing produces a larger value of capacitance C2 for the same dielectric medium, namely, the sample 71 under test. A second reading is taken representing a changed value of capacitance C2 with the predetermined electrode spacing. The difference between these readings is proportional to the moisture, nature of the material and spacings chosen. If the readings are taken over a short period of time any slow drift of the electronics will be nullified since it will be almost the same for each reading.

Thus, data representing the output voltage level of Eref-Esig is taken at two different, but repeatable, electrode spacings. The difference between these two data points is a result which when divided by the sample weight produces a number per unit weight that can be used to calculate the moisture content of the sample. The percent moisture content can be found by the expression:

$$\%MC = A + B * \log(\text{data 1} - \text{data 2})/(\text{sample weight})$$

The constants A and B are obtained empirically during a calibration procedure and will be different for different materials and electrode spacings. The procedure for determining these constants is as follows.

A series of samples are obtained, and weighed. For each sample the value for data 1 and data 2 is determined by the detector 25. A part of the sample is dried in an oven and the actual moisture content is determined. This is done for samples over the range of moisture of interest in the material. When all of the samples have had their actual moisture content determined by drying, this is correlated with the number obtained by taking the log of the difference of the data 1 and data 2 values divided by weight for each sample. The relationship is linear over a range of values and the constant A is the Y intercept and B is the slope of the line. Once the constants A and B are obtained, the percent moisture content of other samples of the same type material are obtained from the constants, the two data values and the sample weight.

During measurement operations, the third, grounded electrode 32 serves a highly useful purpose. In the absence of the third electrode 32, the second electrode 31 would form another unwanted capacitor with the rest of the universe with air and space being the dielectric medium. In practice this additional capacitor is dominated by nearby machinery, wires, cables, etc. The value of this unwanted capacitor is by its nature not well defined and subject to variation. Since we are looking for changes in the impedance dominated by the sample material, then any changes in the unwanted capacitor value will be seen as noise in the measurement. By placing the grounded electrode 32 adjacent to the second electrode 31 on a side away from the sample 71, the unwanted capacitance is controlled and made constant thereby eliminating a source of noise.

Obviously, many modifications and variations of the present invention are possible in light of the above teachings. For example, the reference voltage Eref and signal voltage Esig could be obtained individually and then compared in a separate operation. It is to be understood, therefore, that the invention can be practiced otherwise than as specifically described.

What is claimed is:

1. Apparatus for determining a property of a material by measuring its impedance comprising:
    series circuit means comprising a reference impedance leg and a measurement leg connected in series with said reference impedance leg, and said measurement leg including first and second spaced apart electrodes defining a region for receiving a sample of the material;
    an independent oscillator connected in parallel with said series circuit means;
    output circuit means connected in parallel with said series circuit means and obtaining from said reference impedance leg a reference voltage level and obtaining from said measurement leg a signal voltage level proportional to the impedance of said measurement leg; and
    detector circuit means for combining said reference voltage level and said signal voltage level and producing therewith an output voltage level proportional to said impedance.

2. An apparatus according to claim 1 wherein said oscillator is a crystal oscillator, and including motive means for changing the spacing between said first and second spaced apart electrodes.

3. An apparatus according to claim 1 wherein said reference impedance leg comprises a reference capacitor.

4. An apparatus according to claim 3 wherein said reference impedance leg further comprises a variable resistor.

5. An apparatus according to claim 4 wherein said variable resistor is connected in series with said reference capacitor.

6. An apparatus according to claim 5 wherein said first electrode is grounded.

7. An apparatus according to claim 6 wherein said output circuit means comprises a plurality of reference resistors connected in parallel with said series circuit means, and a plurality of signal resistors connected in parallel with said measurement leg.

8. An apparatus according to claim 7 wherein said detector circuit means comprises differential amplifier means.

9. An apparatus according to claim 8 wherein said detector circuit means further comprises adjustment means for adjusting the magnitude of said output voltage level.

10. An apparatus according to claim 6 including an alternating to direct current converter means and an analog to digital converter means receiving said output voltage level.

11. An apparatus according to claim 1 including motive means for changing the spacing between said first and second spaced apart electrodes.

12. A method for determining a property of a material with a system comprising a series circuit means having a reference impedance leg and a measurement leg connected in series with said reference impedance leg, said measurement leg including first and second spaced apart electrodes defining a region; oscillator circuit means connected in parallel with said series circuit; output circuit means connected in parallel with said series circuit means and obtaining from said reference impedance leg a reference voltage level and obtaining from said measurement leg a signal voltage level proportional to the impedance of said measurement leg; and detector circuit means for combining said reference voltage level and said signal voltage level and producing therewith an output voltage level proportional to a combination of said reference voltage level and said signal voltage level; said method comprising the steps of:

positioning a material sample in said region;

establishing a given spacing between said first and second electrodes;

utilizing said output voltage level to determine an initial impedance of said measurement leg with said given spacing between said first and second electrodes;

establishing a predetermined spacing between said first and second electrodes, said predetermined spacing being different than said given spacing;

utilizing said output voltage level to determine a changed impedance of said measurement leg with said predetermined spacing between said first and second electrodes; and comparing said initial impedance with said changed impedance to determine said property.

13. A method according to claim 12 wherein said comparing stem comprises the step of determining the difference between said initial impedance and said changed impedance.

14. A method according to claim 13 including the steps of determining a value proportional to said difference, determining the weight of said material sample, and dividing said value by said weight.

15. A method according to claim 14 wherein said property is moisture content.

* * * * *